United States Patent [19]

Olmo et al.

[11] Plant 4,866

[45] Jul. 13, 1982

[54] VARIETY OF GRAPEVINE

[75] Inventors: Harold P. Olmo, Davis, Calif.; James F. Guymon, deceased, late of Davis, Calif., by Charlene S. Guymon, executrix

[73] Assignee: The Regents of the University of California, Berkeley, Calif.

[21] Appl. No.: 189,965

[22] Filed: Sep. 22, 1980

[51] Int. Cl.[3] ..... A01H 5/03

[52] U.S. Cl. ..... Plt./47

[58] Field of Search ..... Plt./47

*Primary Examiner*—Robert E. Bagwill

*Attorney, Agent, or Firm*—Townsend and Townsend

[57] ABSTRACT

A new and distinct variety of grapevine of the vinifera species characterized by its early ripening, greater production of sugar and less total acidity than French Colombard. The new variety is useful for production of white table wine but more particularly for distillation and production of high-quality brandy.

3 Drawing Figures

This invention relates to a new and distinct variety of grapevine of the vinifera species to be used for the production of white table wine, but more particularly for distillation and production of high quality brandy.

The new variety is a first generation selection from the cross Semillon×Folle blanche made in 1943 in the vineyards of the University of California, Davis, Calif. The seedling K9-35 was selected as the most promising of 125 vines grown in this progeny and it fruited for the first time at Davis in 1946, later tested under the number B-14 and which has now been named Glennel.

The objectives in breeding this new variety were to produce a variety of distinct fruit composition for the production of high quality brandy. In comparison with the standard variety, French Colombard, often used for brandy production, the new variety ripens earlier and produces more sugar, with less total acidity. It can therefore be harvested before fall rains cause deterioration of the fruit, a serious problem with the French Colombard.

Figure 1:
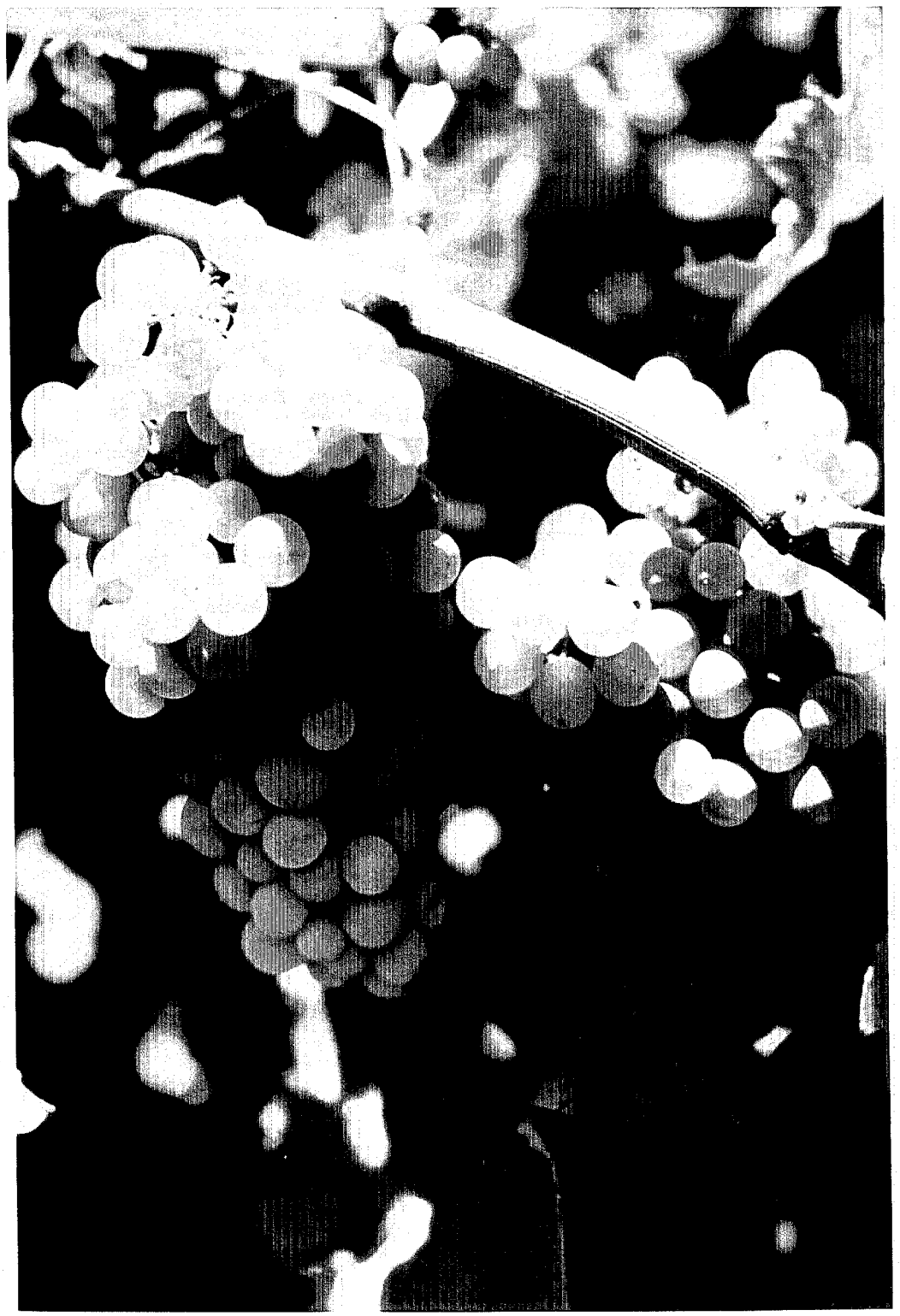
FIG. 1 shows clusters of the grape and the cane typical of the variety.

The selection K9-35 was propagated from the original seedling into a Trial Block at Davis, by field budding to the rootstock Ganzin 1 (Aramon×rupestris) in the fall of 1950. The spacing was 6 feet×12 feet; the vines were trained and pruned to the head form (gobelet). The planting consisted of two replicated and randomized blocks, each variety forming a plot of 10 vines. The three varieties used as controls were Semillon, Folle blanche, and French Colombard.

The first trial block consisted of the best 24 selections from the 125 vine progeny of Semillon×Folle blanche; 6 selections of the cross Semillon×E11-97, and 13 selections of the cross White Riesling×E11-97. The total number of new selections on trial was 43, not including the three control varieties Semillon, Folle blanche and French Colombard.

Two selections were retained for further testing, B-13 and B-14. Forty cuttings of each were planted in the nursery in the spring of 1957. Twenty-two rootings were planted in the vineyard in April, 1958 for further observation.

The new variety is above average in wine quality when made as a dry table wine, but is of most interest for the production of a distinctive, high quality brandy when grown in the warmer parts of the San Joaquin Valley. The vine has excellent recovery after spring frosts as the senescent eyes in the older wood regrow and are highly fruitful.

The variety exhibits high and regular fruitfulness. At Davis during the period 1952–1956, the yield averaged 8.4 tons per acre vs. 8.2 tons per acre for the French Colombard in the same Trial Block. Head pruning was used in this trial. The variety has been indexed for freedom of injurious viruses and is certified for commercial release.

Experimental lots of brandy were distilled by pot process (batch) in 1952 to 1955, then by both pot and continuous still in 1956 and 1957. Some batches were also distilled by vacuum distillation. After sensory evaluations for quality were made on 47 selections and the control varieties French Colombard, Folle blanche and Semillon, the selections B-13 and B-14 were determined as the most promising of the original group.

In April, 1958, the selection B-14 was increased in a larger planting, to supply larger quantities of distillate. Additional brandy trials were undertaken in 1962–1968.

The colors referred to in the following description under the heading "Plant Characteristics" are subject to substantial variation and are not considered distinctive or diagnostic features of the plant of this invention. For this reason, the colors mentioned have not been positively identified.

PLANT CHARACTERISTICS

*Vine.*—Trunk thick, bark shreds and separates early, canes few in number, round in cross-section, with prominent ridges, vigorous canes producing numerous upright laterals, internodes very short, eyes small, prominent, but flattened, bud burst several days after Thompson Seedless.

*Cluster.*—Small, 217 gm., symmetrical, cylindrical to slightly conical, shoulders not prominent, very compact throughout compressing the berries.

Berry slightly ellipsoidal, wt. ten largest berries per cluster=17.5 gms.; pressed out of shape, skin thick and tough, dull greenish-yellow, with heavy bloom, pulp translucent, soft, juicy; shrivels and raisins quickly after full maturity. Early fall rains may cause some fruit spoilage. The peduncle is short, slender, base woody and brown, at right angle to cane, tendril not often present or early dehiscent; if present developing a long slender wing widely branched and separated from the main rachis, pedicels very short, rigid, torus thin, flat; periphery corked over; brush light green, as long as wide, rounded in cross-section, adherence good.

Seeds small, very smooth surface, chalaza very prominent and raised, beak stubbed and cut tangentially to dorsal surface, ventral folds deep and contrasted by light buff color.

Figure 2:
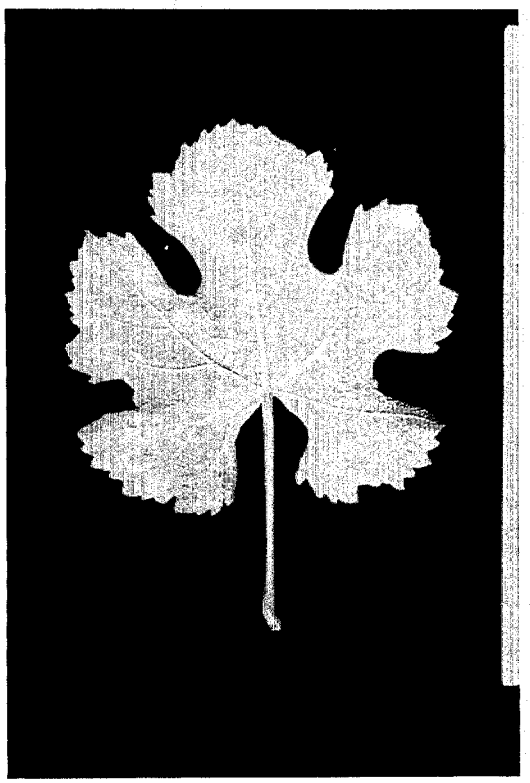
FIG. 2 shows the lower surface of a leaf typical of the variety.
Figure 3:
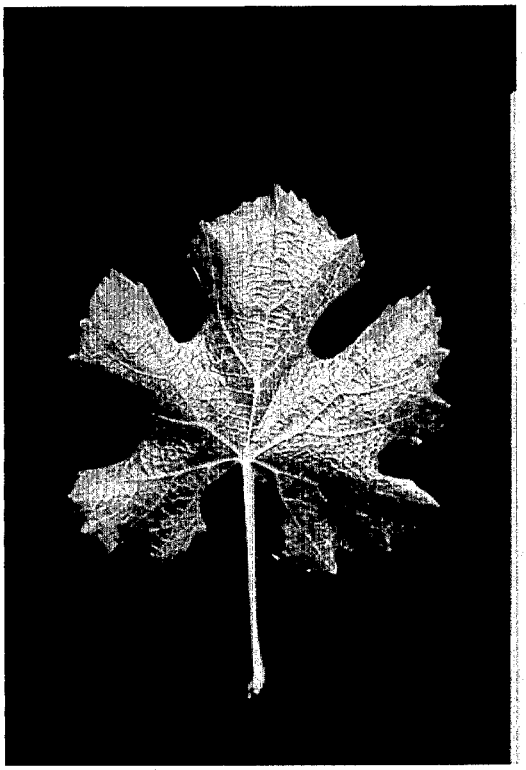
FIG. 3 shows the upper surface of a leaf typical of the variety.

*Leaf.*—(See FIG. 2) Small to medium, as broad as long, outline spherical, upper surface dull green, bullate, petiole slender, very straight, tough; partly suffused wine red on well exposed portions. Lower surface pale green, with long and loose, but fine arachnoid hairiness, dense, but not tufted, some leaves glabrous in appearance to the unaided eye; blade five-lobed, the central lobe very short and blunt, upper sinuses shallow, but straight and very narrow, with parallel sides; lower sinuses about same depth, but about twice as wide and V-shaped, petiolar sinus very wide, open-V, triangular; teeth obtuse, but sharply mucronate, usually in single series on central lobe; petiole thin, 2 mm.; length 64 mm.

Harvest at Davis, Calif. is from the middle to the end of September, when the Brix reaches 22° to 23° and the total acid (as tartaric) ranges from 0.69 to 0.96%. The corresponding ranges for the French Colombard are 20.1° to 22.4° and 0.99 to 1.12%. Thus the new variety ripens earlier and accumulates more sugar, yielding wines 1° to 2° higher in alcohol, and the acid content is considerably lower. The pH ranges are not significantly different.

We claim:

1. The new and distinct grapevine herein described and illustrated, and identified by the characteristics enumerated above.

* * * * *